United States Patent [19]

Helle et al.

[11] Patent Number: 5,350,838
[45] Date of Patent: Sep. 27, 1994

[54] HIGH TEMPERATURE PROCESS FOR PREPARING FIBER REACTIVE DYES

[75] Inventors: Mark A. Helle, Hope; Walter Helmling, West Warwick, both of R.I.

[73] Assignee: Hoechst Celanese Corporation, Somerville, N.J.

[21] Appl. No.: 14,905

[22] Filed: Feb. 8, 1993

[51] Int. Cl.⁵ .............................................. C09B 41/00
[52] U.S. Cl. .................................... 534/638; 534/582; 534/632; 534/642
[58] Field of Search ................ 534/582, 632, 638, 642

[56] References Cited

U.S. PATENT DOCUMENTS

| 4,841,031 | 6/1989 | Kayane et al. | 534/638 |
| 4,937,326 | 6/1990 | Kayane et al. | 534/638 |

FOREIGN PATENT DOCUMENTS

| 59-4653 | 1/1984 | Japan | 534/638 |

*Primary Examiner*—Patricia L. Morris
*Assistant Examiner*—Fiona T. Powers
*Attorney, Agent, or Firm*—Hugh C. Crall

[57] ABSTRACT

A process for preparing monoazo dyes by coupling a aromatic diazonium salt with an amino-4-hydroxy-naphthalene sulfonic acid derivative at a temperature of 40°–85° C. The process of the invention provides a isomerically purer dye.

9 Claims, No Drawings

HIGH TEMPERATURE PROCESS FOR PREPARING FIBER REACTIVE DYES

BACKGROUND OF THE INVENTION

1. Technical Field

The invention relates to a process for preparing fiber reactive dyes.

2. Background

The preparation of fiber reactive dyes based on 6-amino-4-hydroxy-2-naphthalenesulfonic acid and 7-amino-4-hydroxy 2-naphthalenesulfonic acid derivatives is known. These fiber reactive dyes may be represented by the following general formula:

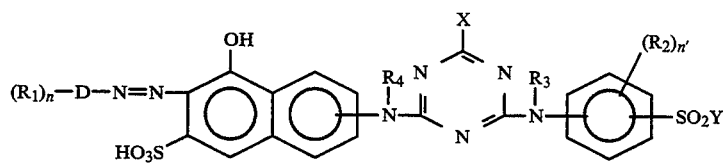

Formula 1 in the above formula, the amino linking group may be in the 6, or 7 ring position on the naphthalene ring. The moiety D represents a phenylene or an naphthylene group. $R_1$ and $R_2$ are independently selected from hydrogen, sulfo, phosphato, carboxy, hydroxy, $C_1$ to $C_4$ alkyl, $C_1$ to $C_4$ alkoxy, aryl and halo; $R_3$ and $R_4$ are independently selected from hydrogen and $C_1$ to $C_4$ alkyl with n and n' are independently equal to an integer of 1 to 3. The moiety X is selected from chloro, fluoro or —NHCN. The moiety $SO_2Y$ is a fiber reactive group wherein Y represents a vinyl group (—CH=$CH_2$) or the moiety —$CH_2$ $CH_2$ Z wherein Z represents a leaving group capable of being split off in an alkaline medium.

The prior art processes for preparing compounds of the above general formula are described in Japanese Patent Publication 59-4653. In one of the prior art processes, the diazo coupling is done at 0°–30° C. In the second process, the amino group on the naphthalenesulfonic acid coupler is acylated with acetic anhydride or acetyl chloride prior to coupling the naphthalenesulfonic acid with the diazonium salt. After the coupling reaction is completed it is necessary to deacylate the reaction product by base-catalyzed high temperature hydrolysis. The deacylated product is then condensed with a fiber reactive anchor moiety e.g. a fiber reactive anchor prepared from the condensation product of aniline-4-(2-sulfatoethyl) sulfone and cyanuric chloride. The reaction sequence is illustrated in FIG. 1.

The acylation-deacylation process of japanese Patent Publication 59-4653 was practiced in the prior art in order to minimize the formation of undesired isomers which are pH sensitive (see e.g. Zollinger, H., Color of Chemistry, Weinheim; New York: VCH, 1987). The isomer depicted in Formula 1 is believed to be the desired product and it is not pH sensitve. In this desired isomer, the diazonium coupling takes place ortho to the hydroxyl group in naphthalenesulfonic acid coupler. However, the prior art coupling reaction of the naphthalene sulfonic coupler (nonacylated) produces appreciable quantities another isomer wherein the diazonium coupling takes place para to isomer, a shift from a yellow shade to a red and dull shade under increasing pH is observed.

The process of the present invention eliminates the need to acylate and deacylate and therefore eliminates undesired formation of acetic acid or sodium acetate by product waste streams which must be treated before discharge to the environment. The process of the invention also provides a method

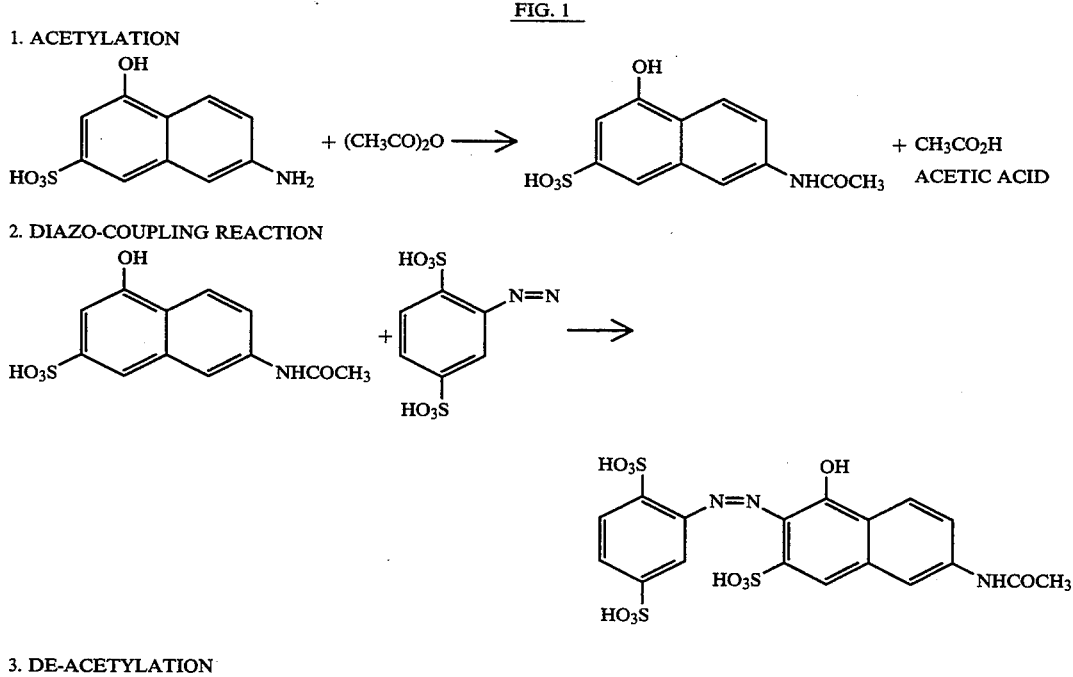

FIG. 1

1. ACETYLATION

2. DIAZO-COUPLING REACTION

3. DE-ACETYLATION

-continued
FIG. 1

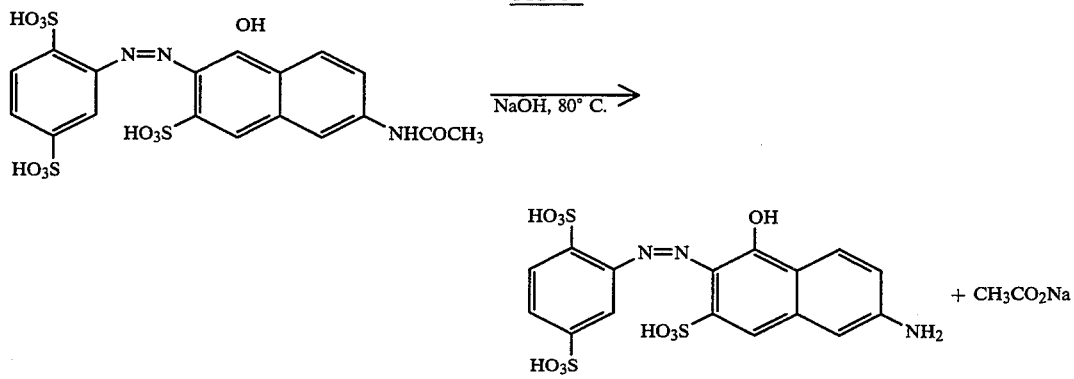

4. PARA-ESTER CONDENSATION

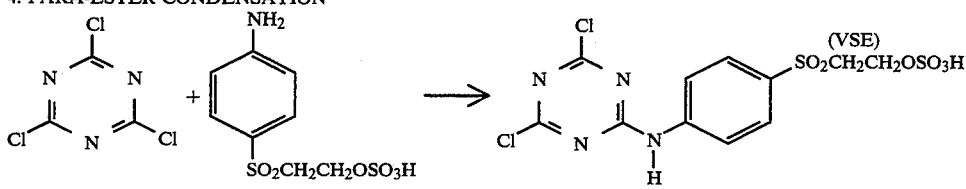

5. FINAL CONDENSATION

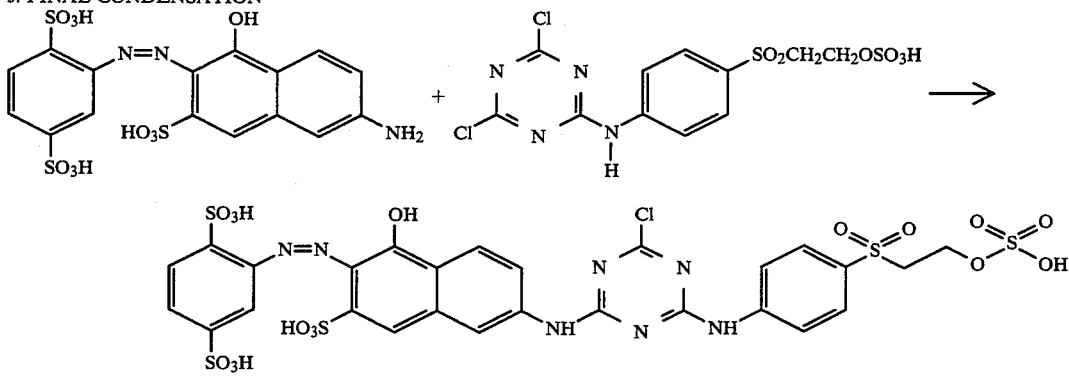

whereby the formation of the undersired para isomer is substantially reduced with an attendant increase in product yield, product quality and process productivity.

SUMMARY OF THE INVENTION

A process for preparing a monoazo dye of the formula:

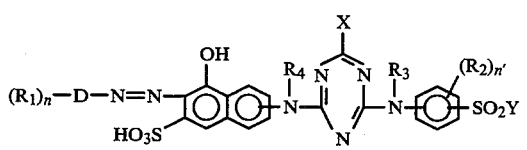

The amino linking may be in the 6 or 7 ring position on the naphthalene ring; the moiety D represent a phenylene or naphthylene group. The groups $R_1$ and $R_2$ are independently selected from hydrogen, sulfo, phosphato, carboxy, hydroxy, $C_1$ to $C_4$ alkyl, $C_1$ to $C_4$ alkoxy, aryl and halogen. The groups $R_3$ and $R_4$ are dependently selected from hydrogen and $C_1$ to $C_4$ alkyl and n and n' are independently an integer from 1 to 3 and; X is selected from chloro, fluoro or —NHCN. Y is —CH=CH$_2$ or —CH$_2$—CH$_2$—Z wherein Z represent a leaving group capable of being split off in an alkaline medium. The invention comprises reacting a diazonium salt of an aromatic amine and a coupling component of an amino-4-hydroxy-2-naphthalene sulfonic acid derivative at a temperature from 40° to 85° C. wherein said diazonium salt has the formula:

wherein D, $R_1$ and n are defined above; and wherein said coupling component has the formula:

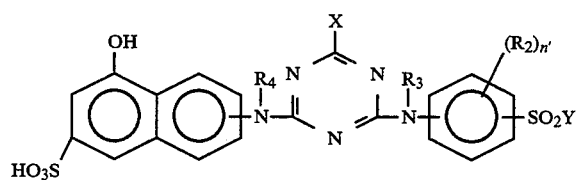

wherein $R_2$, $R_3$, $R_4$, X, Y, n and n' are defined above.

In the process of the invention, an amino-4-hydroxy-2-naphthalenesulfonic acid component is first reacted with the condensation product of an unsubstituted or substituted aniline derivative containing a fiber reactive ring substituent of the vinyl sulfone type and a cyanuric halide or halo-cyanuric cyanoamide. This reaction step eliminates the acylation-deacylation steps of the prior art. The amino-4-hydroxy-2-naphthalenesulfonic acid condensation product is then coupled with a diazonium salt of a phenyl or a naphthyl group at a temperature from about 40°-85° C. This process provides a high quality product substantially free (about 3-6%) of undesired isomers at a low cost.

DESCRIPTION OF THE PREFERRED EMBODIMENTS

This invention is a new and improved process for preparing fiber reactive monoazo dyes based on 6- and 7-amino-4-hydroxy-2 naphthalenesulfonic acid. The invention provides a means for preparing improved dyes of the following formula:

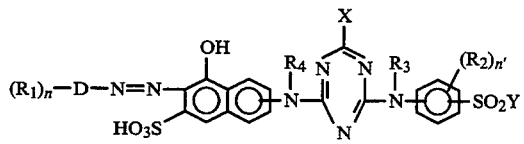

In the above formula, the amino linking group may be in the 6, or 7 ring position on the naphthalene ring. The moiety D represents a phenylene or an naphthylene group; $R_1$ and $R_2$ are independently selected from hydrogen, sulfo, phosphato, carboxy, hydroxy, $C_1$ to $C_4$ alkyl, $C_1$ to $C_4$ alkoxy, aryl and halogen; $R_3$ and $R_4$ are independently selected from hydrogen and $C_1$ and $C_4$ alkyl with n and n' independently an integer of 1 to 3. The moiety X is selected from chloro, fluoro or —NHCN. The moiety $SO_2Y$ is a fiber reactive group wherein Y represents a vinyl group (—CH=CH$_2$) or the moiety —CH$_2$ CH$_2$ Z wherein Z represents an organic or inorganic leaving group capable of being split off in an alkaline medium. Y is preferably the sulfatoethyl group and X is preferably chloro.

The moiety Z may be a halogen atom, preferably chlorine or bromine, a lower ($C_1$ to $C_6$) alkylsulfonyloxy or alkylsulfonylamino group, a ($C_6$ to $C_{10}$) arylsulfonyloxy group, an ($C_6$ to $C_{10}$) arylsulfonylamino group, a lower ($C_1$ to $C_7$) acyloxy group, for example, the acetoxy or benzoyloxy group, a phenoxy group, a ($C_1$ to $C_4$) dialkylamino group, preferably a dimethyl or diethylamino group, a trialkylammonium group, especially the thiosulfato group—SSO$_3$H, the phosphate group—OPO$_3$H$_2$ and, most preferably, the sulfato group—OSO$_3$H. The term acyl as used in this description means the group "RCO-" wherein R is a $C_1$ to $C_6$ alkyl or a phenyl group.

The improved process of the invention comprises the direct coupling of an amino-4-hydroxy-2-naphthalenesulfonic acid derivative with a naphthyl or phenyl diazonium salt at a temperature of about 40°-85° C. This high temperature coupling process produces a dye that is substantially free (about 3-6%) of undesired alkaline sensitive isomers; i.e. isomers that undergo a color shift under alkaline pH conditions. The quality of the products of the process of the invention is more consistent and a dye yield approximately 20% higher than the prior art process is attained. The invention also provides a more efficient manufacturing procedure by eliminating the acylation-deacylation steps of the prior art. In addition, the process of the invention is more environmentally sound and more cost efficient in that it provides a reduction in waste streams and reduced consumption of energy and raw materials.

The coupling component used in the process of the invention may be represented by the following formula:

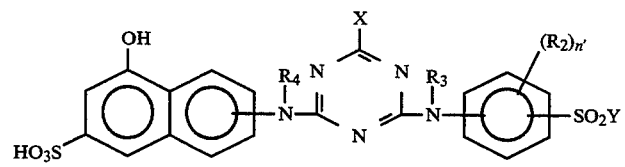

FORMULA 2 where the substitutents $R_2$, $R_3$, $R_4$, X and Y are defined above. The methods for preparation of coupling components of Formula 2 are well known in the art (see for e.g. U.S. Pat. No. 4,701,523). A cyanuric halide or a halo-cyanuric cyanamide is reacted with a substituted aniline containing a fiber reactive substituent of the vinyl sulfone type (—SO$_2$—Y). The resulting condensation product is then condensed with the amino-4-hydroxy-naphthalenesulfonic acid component to provide the coupling component of Formula 2. The order of condensing the reactants is optional as will be readily apparent to the skilled worker.

Exemplary substitued anilines useful in the process of the invention are:
4-(beta-sulfatoethylsulfonyl)-phenyl-amino,
3-(beta-sulfatoethylsulfonyl)-phenyl-amino,
4-(beta-sulfatoethylsulfonyl)-2-sulfo-phenyl-amino,
4-(beta-sulfatoethylsulfonyl)-phenyl-amino-2-methoxy-5-methyl,
4-(beta-sulfatoethylsulfonyl)-phenyl-amino-2,5-dimethoxy,
5-(beta-sulfatoethylsulfonyl)-phenyl-amino-2-methoxy,
3-(beta-sulfatoethylsulfonyl)-4-(N-beta-sulfatoethyl-N-methyl-amino)phenylamino,
3,4-bis-(beta-sulfatoethylsulfonyl)-phenyl-amino,
3-(beta-sulfoatethylsulfonyl)-4-methoxy-phenyl-amino,
4-(beta-sulfatoethylsulfonyl)-phenyl-N-methyl-amino,
3-(beta-sulfatoethylsulfonyl)-4-sulfo-phenyl-amino,
4-(beta-sulfatoethylsulfonyl)-phenyl-N-ethyl-amino,
3-(beta-sulfatoethylsulfonyl)-phenyl-N-ethyl-amino, and
3-(beta-sulfatoethylsulfonyl)-phenyl-N-methyl-amino.

The diazonium salt useful in the process of the invention is prepared from aromatic amines of the general formula $(R_1)_n$—D—NH$_2$ by techniques well known in the art. Exemplary aromatic amines are: 1-aminobenzene-2-sulfonic acid, 1-aminobenzene-3- and -4-sulfonic acid, 2-amino-4-sulfobenzoic acid, 2-amino-5-sulfobenzoic acid, 4-amino-2-sulfobenzoic acid, 4-aminotoluene-2- and -3-sulfonic acid, 2-aminotoluene-4- and -5-sulfonic acid, 2-aminotoluene-4-carboxylic acid, anthranilic acid, 2-aminoanisole-4- and -5-sulfonic acid, 4-amino-anisole-2- and -3-sulfonic acid, 3-chloro-2-amino-3-toluene-5-sulfonic acid, 1-aminobenzene-2,5-disulfonic acid, 1-aminobenzene-2,4- and -3,5-disulfonic acid, 2-aminotoluene-3,5-disulfonic acid, 2-aminotoluene-4,5 and -4,6-disulfonic acid, 4-aminotoluene-2,5-disulfonic acid, 2-aminonaphthalene-1-sulfonic acid, 2-aminonaphthalene-5- and -6-sulfonic acid, 2-aminonaphthalene-7- and -8-sulfonic acid, 1-aminonaphthalene-2, -3-, -4-, -5-, -6-, -7- and -8-sulfonic acid, 2-aminonaphthalene-4,8-disulfonic acid, 2-aminonaphthalene-6,8-disulfonic acid, 2-aminonaphthalene-1,5 and -1,7-disulfonic acid, 2-aminonaphthalene-5,7-, -3,6-, -3,7- and -4,7-disulfonic acid, 1-aminonaphthalene-2,4, -2,5-, -3,6-, -3,7-, -3,8-, -4,6-, -4,7-, -4,8-, -5,7- and -6,8-disulfonic acid, 2-aminonaphthalene-3,6,8-trisulfonic acid, 2-aminonaphthalene-4,6,8-and 1,5,7-trisulfonic acid, 1-aminonaphthalene-2,4,7-sulfonic acid, 1-aminonaphthalene-2,4,8-, -3,5,7-, -3,6,8- and -4,6,8-trisulfonic acid.

Exemplary preferred aromatic amines useful in practice of the invention are:
aniline-2,5 disulfonic acid,
aniline-2-sulfonic acid,
2-naphthylamine-1,5-disulfonic acid,
aniline-2,4 disulfonic acid,
p-anisidine-2,5 disulfonic acid, and
p-anisidine-2-sulfonic acid.

The para isomer of the coupling reaction of a Formula 2, 6-amino-4-hydroxy-2-naphthalenesulfonic acid derivative with a diazonium salt of an aniline-2,5 disulfonic acid is undesired because of its pH sensitivity. In this discussion para isomer means the position isomer of the FIG. 1 compound wherein the diazonium salt is coupled para to the hydroxy group of the naphthalenesulfonic acid moiety. The formation of this undesired para isomer has been found to be extremely temperature dependent. When the diazo-coupling reaction of the 6-amino-4-hydroxy-2-naphthalenesulfonic acid derivative is conducted at 0° C., the amount of para isomer formed is about 30%. Increasing the coupling reaction temperature to 20° C. resulted in the formation of 13% (Area % by HPLC ($\lambda$-298 nm) of the para isomer. This level of undesired by product is still sufficient to cause a dramatic shift in shade under alkaline conditions. When the diazonium coupling is done at 65° C., the amount of undesired para isomer is reduced to about 3–5% and at this level an alkaline shade shift is not visibly noticeable. The diazonium coupling reaction is conducted in the process of the invention at a reaction temperature from about 40° to 85° C., preferably about 60°–70° C.

The following examples are illustrative of the invention and are not intended to limit the scope of the invention or the claims hereto. In the following the % para-isomer is reported in area percentages as determined by HPLC ($\lambda$-298 nm).

EXAMPLE 1

A solution of aniline-4-(2-sulfatoethyl) is condensed with cyanuric chloride (1,3,5 trichlorotriazine) at 0°–25° C. while maintaining the pH of the slurry at 2.0–7.0 with the constant addition of an inorganic base. When the reaction is complete, 6-amino-4-hydroxy-2-naphthalenesulfonic acid is added and the second condensation is stirred at 10°–30° C. while maintaining the pH at 2.0–7.0 by the constant addition of an inorganic base. When the reaction is completed, the solution is heated to 30°–75° C. in preparation for the coupling reaction.

In a separate vessel, a cold acidic slurry of aniline 2,5 disulfonic acid (0°–5° C., pH <1.5) is diazotized by the slow addition of sodium nitrite. Excess sodium nitrite is destroyed by the addition of sulfamic acid. The resulting diazonium salt is added to the heated solution of 2-chloro-4-[N-aniline-4-(2-sulfatoethylsulfone)]-6-[N-6-amino-4-hydroxy-2-naphthalenesulfonic acid]-1,3,5 triazine while maintaining the pH at 3.5–4.0 with the addition of an inorganic base and the temperature at about 0° C. The para isomer content is 26.6% and the reaction product produces a golden orange shade with poor shade qualities at high pH.

EXAMPLE 2

This experiment is conducted substantially in accordance with the process of Example 1 except that the coupling reaction was conducted at 20° C. The para isomer content is 12.3%. The reaction product produces a golden-orange shade. The reaction product also produced a golden-orange shade with poor shade qualities at a high pH.

EXAMPLE 3

This experiment is conducted substantially in accordance with the process of Example 1 except that the coupling reaction was conducted at 40° C. The para isomer content is 6.6%. The reaction product gave a golden-orange shade with good shade qualities and high shade stability over varying pH conditions.

EXAMPLE 4

This experiment is conducted substantially in accordance with the process of Example 1 except that the coupling reaction was conducted at 65° C. The para isomer content is 5.1%. The reaction product gave a golden-orange shade with good shade qualities and high shade stability over varying pH conditions.

EXAMPLE 5

This experiment is conducted substantially in accordance with the process of Example 1 except that the coupling reaction was conducted at 85° C. The para isomer content is 3.6%. The reaction product gave a golden-orange shade with good shade qualities and high shade stability over varying pH conditions.

The following Table 1 summarizes the amount of para isomer formation versus temperature when Example 1 is repeated at different temperatures.

TABLE 1

| Temperature °C. | Para-Isomer % Area |
| --- | --- |
| 0 | 28.6 |
| 20 | 12.3 |
| 40 | 6.6 |
| 65 | 5.1 |
| 85 | 3.6 |

Dyes prepared according to the present invention are suitable for the dyeing of cellulosic materials such as cotton, linen, viscose rayon or staple fibers. They can be applied by any one of the usual dyeing and printing methods for reactive dyestuffs and yield on cellulosic materials, in the presence of alkaline agents, brilliant shades having excellent fastness properties, and high color yield and reduced cold water bleeding. These dyes may also be used on wool, silk or polyamide fibers.

We claim:

1. A process for preparing a monoazo dye of the formula:

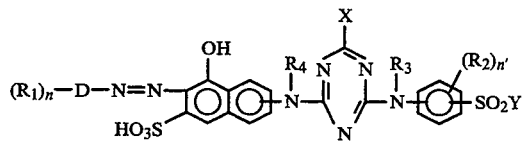

wherein the amino linking group may be in the 6, or 7 ring position on the naphthalene ring; the moiety D represent a phenylene or naphthylene group; $R_1$ and $R_2$ are independently selected from hydrogen, sulfo, phosphato, carboxy, hydroxy, $C_1$ to $C_4$ alkyl, $C_1$ to $C_4$ alkoxy, aryl and halogen; $R_3$ and $R_4$ are independently selected from hydrogen and $C_1$ to $C_4$ alkyl and n and n' are independently an integer from 1 to 3; X is selected from chloro, fluoro or —NHCN; Y is —CH=$CH_2$ or —$CH_2$—$CH_2$—Z wherein Z represent a leaving group capable of being split off in an alkaline medium which comprises contacting a diazonium salt of an aromatic amine and a coupling component of an amino-4-hydroxy-2-naphthalene sulfonic acid derivative at a temperature from 60° to 85° C. wherein said diazonium salt has the formula:

wherein D, $R_1$ and n are defined above; and wherein said a coupling component has the formula:

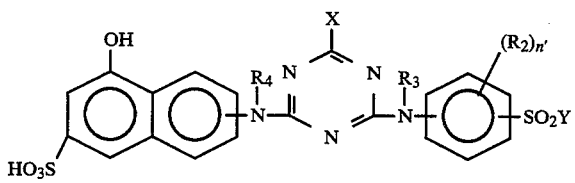

wherein $R_2$, $R_3$, $R_4$, X, Y and n' are defined above.

2. A process according to claim 1 where said temperature is from about 60° to 70° C.

3. A process according to claim 1 wherein $R_1$ is sulfo; n is 1 or 2; $R_2$, $R_3$, $R_4$ are hydrogen and n' is 1.

4. A process according to claim 1 wherein said diazonium salt is selected from the group consisting of diazotized:
aniline-2,5 disulfonic acid,
aniline-2-sulfonic acid,
2-naphthylamine-1,5-disulfonic acid,
anlline-2,4 disulfonic acid,
p-anisidine-2,5 disulfonic acid, and
p-anisidine-2-sulfonic acid.

5. A process according to claim 1 wherein said amino linking group is in the sixth ring position.

6. A process according to claim 1 wherein the moiety $SO_2Y$ is a beta-sulfatoethyl sulfonyl group.

7. A process according to claim 1 wherein said monoazo dye has the formula:

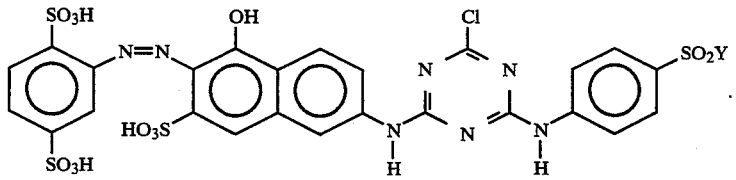

8. A process according to claim 1 wherein said monoazo dye has the formula:

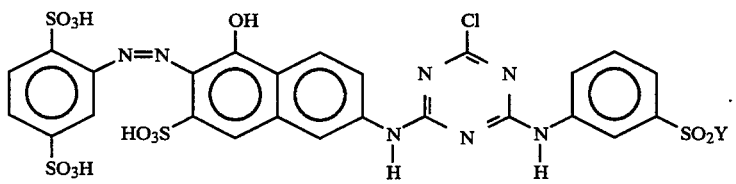

9. A process according to claim 1 wherein said monoazo dye has the formula:

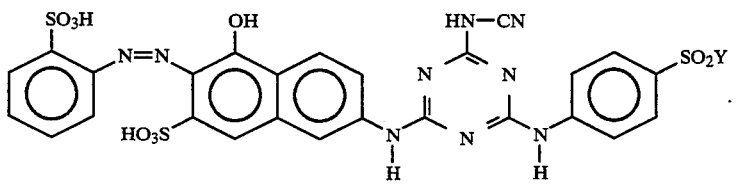

* * * * *